United States Patent
Shoji et al.

(10) Patent No.: US 7,169,746 B2
(45) Date of Patent: Jan. 30, 2007

(54) PERFUME COMPOSITION

(75) Inventors: Ken Shoji, Kanagawa (JP); Tatsushi Horita, Kanagawa (JP); Sumie Taguchi, Yokohama (JP); Masanori Yoshimura, Yokohama (JP); Keiko Sakai, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 10/486,107

(22) PCT Filed: Mar. 26, 2002

(86) PCT No.: PCT/JP02/02908

§ 371 (c)(1),
(2), (4) Date: Jul. 21, 2004

(87) PCT Pub. No.: WO02/053151

PCT Pub. Date: Jul. 11, 2002

(65) Prior Publication Data

US 2004/0242452 A1   Dec. 2, 2004

(30) Foreign Application Priority Data

Aug. 8, 2001 (JP) .............................. 2001-240499
Aug. 8, 2001 (JP) .............................. 2001-240500

(51) Int. Cl.
*A61K 8/18* (2006.01)
(52) U.S. Cl. ........................................................ 512/1
(58) Field of Classification Search ...................... 512/1
See application file for complete search history.

(56) References Cited

U.S. PATENT DOCUMENTS 3,993,604 A * 11/1976 Thomas et al. ............. 426/538

6,268,333 B1 * 7/2001 Okazaki et al. ............... 512/20

FOREIGN PATENT DOCUMENTS

| CH | 565 515 A | 8/1975 |
|----|-----------|--------|
| GB | 1 401 747 A | 7/1975 |
| GB | 2 004 462 A | 4/1979 |
| JP | 06-172781 | 6/1994 |

OTHER PUBLICATIONS

First Office Action dated Apr. 15, 2005 for counterpart Chinese application, and English translation thereof.

(Continued)

*Primary Examiner*—Monique T. Cole
(74) *Attorney, Agent, or Firm*—Townsend & Banta

(57) ABSTRACT

The present invention provides a perfume composition for mental control, the composition containing one or more components acknowledged as having a psycho-sedative effect selected from the group consisting of terpinyl butyrate, γ-nonalactone, acetyl isoeugenol, methyl anisate, terpineol, nerol, chrysanthenone, lyral, lilial, β-phenylethyl alcohol, γ-methyl ionone, Iso E Super, Z-3-hexenyl salicylate, p-methylphenylacetaldehyde, limonene, ocimene, helional, linalyl acetate, geranyl acetate, geraniol, hedione, linalool, citronellol, and γ-hexalactone and/or one or more components acknowledged as having a psycho-stimulative effect selected from the group consisting of piperitone, isoamyl angelate, phenylethyl angelate, cuminyl alcohol, menthalactone, ethyl myristate, and perilla aldehyde. The invention also provides an external composition and daily-use goods, containing the perfume composition for mental control.

2 Claims, 3 Drawing Sheets

OTHER PUBLICATIONS

Patent Abstracts of Japan, JP 2000-154394 dated Jun. 6, 2000 and English Abstract thereof.
"The Exploitation, Research And Progress of Perilla Plant", from "The Journal of Wuhan Polytechnic University".
Database WPI, Section Ch, Week 199336, Derwent Publications Ltd., XP002362532 & JP 05 202380 A, Aug. 10, 1993.
JP 1-254629, Oct. 11, 1989, & English Abstract thereof.

Z Naturforsch Nov.-Dec., 46(11-12), 1067-72, 1991.

Chem. Senses 26, 239-245, 2001.

* cited by examiner

PERFUME COMPOSITION

TECHNICAL FIELD

The present invention relates to a perfume exerting a specific psychological effect, and more particularly, to a perfume for effecting mental control through psycho-sedation or psycho-stimulation.

BACKGROUND ART

Various studies have elucidated that a variety of stresses exhibit diverse physiological and psychological effects on different individuals. Particularly, in modern society, which is sometimes referred to as "stressful society," coping with the variety of stresses is a critical issue.

Among countermeasures against stress, a typical measure is mental control, including mental sedation or mental stimulation, which seem to contrast with each other.

Mental sedation is considered to be a typical mode of mental control for mitigating, through psychological healing, adverse mental conditions affected by stress.

In recent years, aromatherapy has become of keen interest as mental sedation means. In aromatherapy, essential oils such as lavender oil and chamomile oil have conventionally been confirmed to exhibit mental sedative effects in folk medicine. These essential oils are advantageous in that they provide a desired sedative effect in a considerably mild manner, since they exert mental sedative effects on the basis of the aroma thereof.

Mental stimulation is considered to be a typical mode of mental control for mitigating depressive conditions caused by stress.

In recent years, the aforementioned aromatherapy has also attracted attention as means for mitigating depressive conditions. Specifically, attempts have been made to mitigate depressive conditions by use of natural fragrances which according to folklore are known to have an arousal effect so as to provide a mental stimulative effect.

However, selection and formulation of natural fragrances which are used to provide a mental sedative effect or a mental stimulative effect are highly dependent on empirical knowledge of skilled aromatherapists, and these effects have not been completely elucidated. This may be largely attributed to the fact that natural fragrances such as essential oils used in aromatherapy are composed of many components of different types.

Regarding such components, Japanese Patent Application Laid-Open (kokai) No. 6-172781 discloses that 1,3-dimethoxy-5-methylbenzene has a sedative effect; that the sedative effect is also expressed through inhalation of a vaporized perfume or similar material to which the compound has been added; and that the compound can be added to a variety of perfumes by virtue of its mild aroma so as to provide a mental sedative effect.

In order to obtain a stimulative effect more generally, studies have been carried out for identifying a component which exerts the stimulative effect and for producing a perfume composition to which the component has been incorporated. For example, Japanese Patent Application Laid-Open (kokai) No. 1-254629 discloses that a certain fraction obtained through distillation of lemon oil under reduced pressure, the lemon oil being, according to folklore, acknowledged to have a mental stimulative effect, can elevate the level of consciousness; and that the mental stimulative effect can be exerted through inhalation of a vaporized perfume composition or similar material to which the fraction has been added. Japanese Patent Application Laid-Open (kokai) No. 11-196295 discloses that anisaldehyde—a single compound—is acknowledged to have a mental stimulative effect; and that a perfume composition to which the compound has been added exhibits a similar stimulative effect.

However, in order to actually obtain a mental sedative or stimulative effect in various scenes of daily life or in aromatherapy, formulation of such compositions must be determined simply and appropriately, in response to fragrance preferences of many people and to compatibility with a variety of co-used perfumes which people wear or use in a variety of situations of daily life. Therefore, it is required to find out substances which can attain mental control by exerting a variety of mental sedative or stimulative effects.

In addition, another essential requirement is to identify a number of components which exert a variety of mental sedative or stimulative effects, in order to attain mental control through incorporation of the components into a variety of perfume compositions or similar materials without greatly affecting the base aroma of the compositions or materials.

Thus, an object of the present invention is to find out a novel component having a mental control action such as a mental sedative action or a mental stimulative action and to produce a perfume composition for mental control containing such a novel component.

DISCLOSURE OF THE INVENTION

In order to attain the above object, the present inventors have carried out extensive studies on a large number of components in terms of mental control effect, and have found that, among components contained in natural essential oils, terpinyl butyrate, γ-nonalactone, acetyl isoeugenol, methyl anisate, terpineol, nerol, chrysanthenone, lyral, lilial, β-phenylethyl alcohol, γ-methyl ionone, Iso E Super, Z-3-hexenyl salicylate, p-methylphenylacetaldehyde (also called syringa aldehyde), limonene, ocimene, helional, linalyl acetate, geranyl acetate, geraniol, hedione (also called methyl dihydrojasmonate), linalool, citronellol, and γ-hexalactone are acknowledged to have a mental sedative effect (hereinafter may be referred to as "psycho-sedative effect"), and that, among components contained in natural essential oils, piperitone, isoamyl angelate, phenylethyl angelate, cuminyl alcohol, menthalactone, ethyl myristate, and perilla aldehyde are acknowledged to have a mental stimulative effect (hereinafter may be referred to as "psycho-stimulative effect"). The present invention drawn to a psycho-controlling perfume composition has been accomplished on the basis of these findings.

Accordingly, the present invention provides a psycho-controlling perfume composition (hereinafter may be referred to as a psycho-controlling composition) comprising one or more components selected from the group consisting of terpinyl butyrate, γ-nonalactone, acetyl isoeugenol, methyl anisate, terpineol, nerol, chrysanthenone, lyral, lilial, β-phenylethyl alcohol, γ-methyl ionone, Iso E Super, Z-3-hexenyl salicylate, p-methylphenylacetaldehyde, limonene, ocimene, helional, linalyl acetate, geranyl acetate, geraniol, hedione, linalool, citronellol, and γ-hexalactone and/or one or more components selected from the group consisting of piperitone, isoamyl angelate, phenylethyl angelate, cuminyl alcohol, menthalactone, ethyl myristate, and perilla aldehyde.

In the present invention, the term "psycho-controlling perfume composition" refers to a perfume composition which, directly or indirectly, can control to a favorable state the mental conditions of a person using the composition. When the psycho-controlling perfume composition is incorporated into objects such as compositions for external use (hereinafter referred to as external compositions) (e.g., cosmetics), daily-use goods (e.g., room deodorants and aroma candles), and food compositions, the psycho-controlling perfume composition can impart a mental control action to these objects. Specifically, when a user inhales an effective component of the present psycho-controlling composition by the mediation of an object containing the psycho-controlling composition, stimulation of the olfactory receptors or absorption of the component by the body via the respiratory tract occurs, whereby the user receives a mental control effect. As mentioned above, a typical, specific mode of a mental controlling effect includes a mental sedative effect or a mental stimulative effect. The present invention also provides a perfume composition on the basis of the specific mode.

Specifically, the present invention provides a psycho-sedative perfume composition (hereinafter may be referred to as a psycho-sedative composition) comprising one or more components selected from the group consisting of terpinyl butyrate, γ-nonalactone, acetyl isoeugenol, methyl anisate, terpineol, nerol, chrysanthenone, lyral, lilial, β-phenylethyl alcohol, γ-methyl ionone, Iso E Super, Z-3-hexenyl salicylate, p-methylphenylacetaldehyde, limonene, ocimene, helional, linalyl acetate, geranyl acetate, geraniol, hedione, linalool, citronellol, and γ-hexalactone.

In the present invention, the term "psycho-sedative perfume composition" refers to a perfume composition which can mentally sedate a user by use thereof, thereby imparting a relaxed feeling to the user. The psycho-sedative perfume composition can impart a mental sedative action to products, through incorporation into the products such as external compositions (e.g., cosmetics), daily-use goods (e.g., room deodorants and aroma candles), and food compositions. The term "psycho-sedative effect" refers to an effect of releasing physiological/psychological mal-conditions such as nervous conditions and excitation which humans experience in daily life, thereby providing a relaxed feeling. The psycho-sedative effect can be confirmed by a sensory test of panelists or on the basis of an index (e.g., CNV measurements) which can detect mental sedation feeling.

The present invention also provides a psycho-stimulative perfume composition (hereinafter may be referred to as a psycho-stimulative composition) comprising one or more components selected from the group consisting of piperitone, isoamyl angelate, phenylethyl angelate, cuminyl alcohol, menthalactone, ethyl myristate, and perilla aldehyde.

In the present invention, the term "psycho-stimulative perfume composition" refers to a perfume composition which can impart a mental uplifting feeling to a user by use thereof. The psycho-stimulative perfume composition can impart a mental stimulation action to products, through incorporation into the products such as external compositions (e.g., cosmetics), daily-use goods (e.g., room deodorants and aroma candles), and food compositions. The term "psycho-stimulative effect" refers to an effect of alleviating physiological/psychological mal-conditions such as sleepiness, fatigue, and dull feeling, which humans experience in daily life, thereby refreshing the feeling and activating mental action. The psycho-stimulative effect can be confirmed by a sensory test of panelists or on the basis of an index (e.g., CNV measurements) which can detect a mental uplifting feeling.

EMBODIMENT FOR CARRYING OUT THE INVENTION

Figure 1:
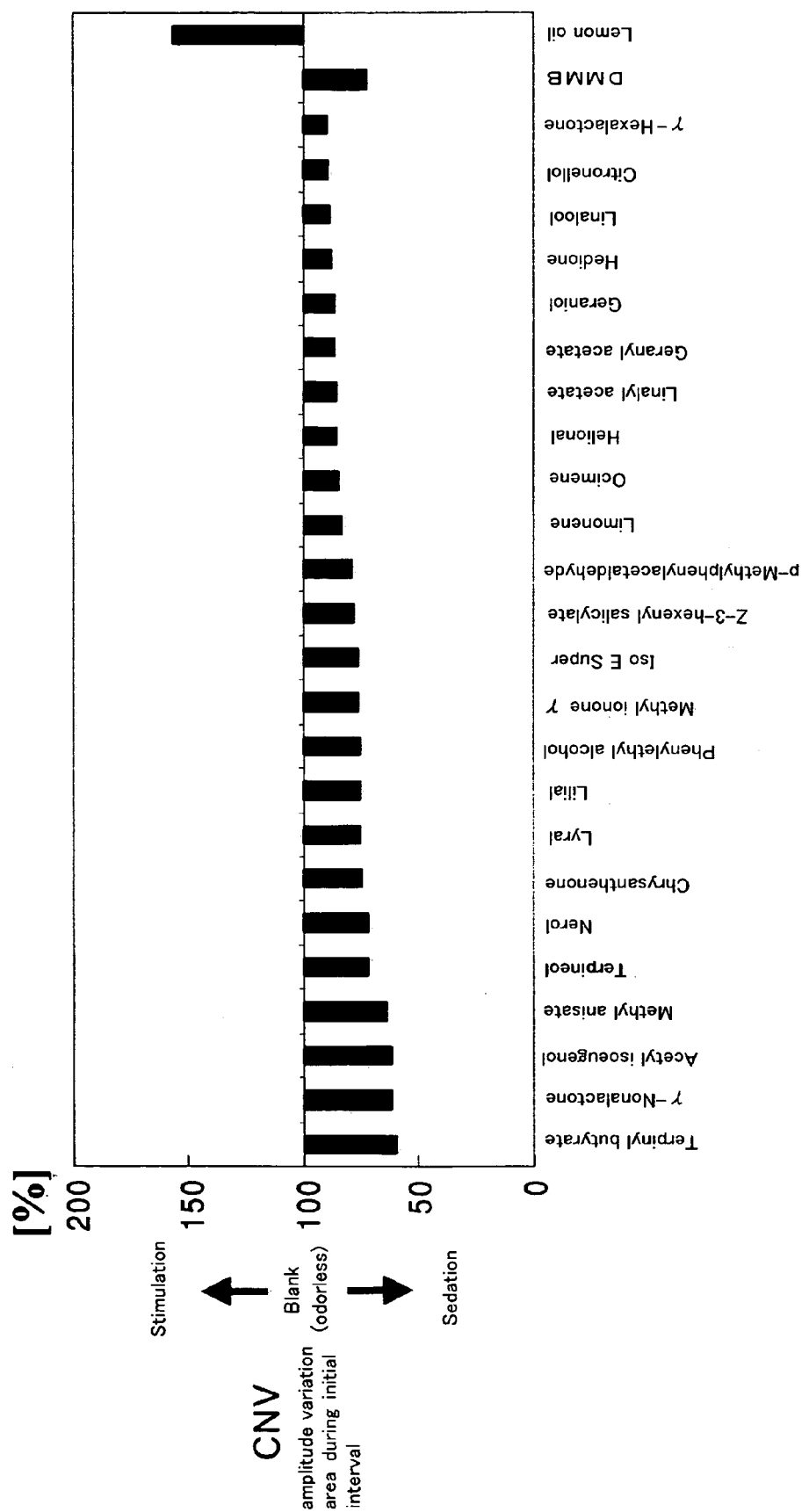
FIG. 1 is a graph showing measured CNV values of components contained in the psycho-controlling composition which can be employed as the psycho-sedative composition.

Embodiments for carrying out the invention will next be described.

1. Among components contained in the psycho-controlling composition, components having a psycho-sedative effect; i.e., components which can be employed as the psycho-sedative components of the psycho-sedative composition will be described.

Terpinyl butyrate, which is a component of the psycho-controlling composition and has a psycho-sedative effect, is known to have a rosemary-like balsamic and floral aroma. In the present invention, either terpinyl butyrate which has been produced through a routine method or a commercial terpinyl butyrate product can be employed.

γ-Nonalactone is known to have a creamy coconut aroma. In the present invention, either γ-nonalactone which has been isolated from an essential oil such as peach oil and purified through a routine method or a commercial γ-nonalactone product can be employed.

Acetyl isoeugenol (i.e., methoxy-4-acetoxypropenylbenzene) is known to have a balsamic, perilla-like, and carnation-like sweet floral note. In the present invention, either acetyl isoeugenol which has been produced through a routine method or a commercial acetyl isoeugenol product can be employed.

Methyl anisate is known to have a sweet herbal anis aroma, impressing lilac or magnolia aroma. In the present invention, either methyl anisate which has been produced through a routine method or a commercial methyl anisate product can be employed.

Terpineol is known to have a lilac-like aroma. In the present invention, either terpineol which has been isolated from an essential oil such as orange oil and purified through a routine method or a commercial terpineol product can be employed.

Nerol is known to have an aroma similar to that of geraniol. In the present invention, either nerol which has been isolated from an essential oil such as neroli oil and purified through a routine method or a commercial nerol product can be employed.

Chrysanthenone is known to have a metalic herbal green aroma. In the present invention, either chrysanthenone which has been isolated from an essential oil such as artemisia oil and purified through a routine method or a commercial chrysanthenone product can be employed.

Lyral is known to have a lily-like aroma. In the present invention, either lyral which has been produced through a routine method or a commercial lyral product can be employed.

Lilial is known to have a lily-like aroma. In the present invention, either lilial which has been produced through a routine method or a commercial lilial product can be employed.

β-Phenylethyl alcohol is known to have a gentle rose-like aroma. In the present invention, either β-phenylethyl alcohol which has been isolated from an essential oil such as rose oil and purified through a routine method or a commercial β-phenylethyl alcohol product can be employed.

γ-Methyl ionone is known to have a gentle violet-like and orris-like aroma. In the present invention, either γ-methyl ionone which has been produced through a routine method or a commercial γ-methyl ionone product can be employed.

Iso E Super is known to have a woody/amber-like aroma. In the present invention, either Iso E Super which has been produced through a routine method or a commercial Iso E Super product can be employed.

Z-3-Hexenyl salicylate (i.e., cis-3-hexenyl salicylate) is known to have a balsamic/floral-like aroma. In the present invention, either Z-3-hexenyl salicylate which has been produced through a routine method or a commercial Z-3-hexenyl salicylate product can be employed.

p-Methylphenylacetaldehyde is known to have a fruity green aroma. In the present invention, either p-methylphenylacetaldehyde which has been isolated from an essential oil such as corn oil and purified through a routine method or a commercial p-methylphenylacetaldehyde product can be employed.

Limonene is known to have a fresh citrus-like aroma. In the present invention, either limonene which has been isolated from an essential oil such as orange oil and purified through a routine method or a commercial limonene product can be employed.

Ocimene is known to have a green woody herbal aroma, impressing anis or citrus lime aroma. In the present invention, either ocimene which has been isolated from an essential oil such as thyme oil and purified through a routine method or a commercial ocimene product can be employed.

Helional is known to have a sweet heliotrope-like and anis-like floral aroma. In the present invention, either helional which has been produced through a routine method or a commercial helional product can be employed.

Linalyl acetate is known to have a fresh sweet fruity/floral aroma. In the present invention, either linalyl acetate which has been isolated from an essential oil such as lavender oil and purified through a routine method or a commercial linalyl acetate product can be employed.

Geranyl acetate is known to have a sweet rose-like aroma. In the present invention, either geranyl acetate which has been isolated from an essential oil such as lemon oil and purified through a routine method or a commercial geranyl acetate product can be employed.

Geraniol is known to have a rose-like aroma. In the present invention, either geraniol which has been isolated from an essential oil such as geranium oil and purified through a routine method or a commercial geraniol product can be employed.

Hedione is known to have a jasmine-floral aroma. In the present invention, either hedione which has been isolated from an essential oil such as jasmine oil and purified through a routine method or a commercial hedione product can be employed.

Linalool is known to have a lily-like aroma. In the present invention, either linalool which has been isolated from an essential oil such as orange oil and purified through a routine method or a commercial linalool product can be employed.

Citronellol is known to have a fresh rose-like aroma. In the present invention, either citronellol which has been isolated from an essential oil such as rose oil and purified through a routine method or a commercial citronellol product can be employed.

γ-Hexalactone is known to have a mild herbal, tobacco-like, and coumarin-like aroma. In the present invention, either γ-hexalactone which has been isolated from an essential oil such as apricot oil and purified through a routine method or a commercial γ-hexalactone product can be employed.

2. Among components contained in the psycho-controlling composition, components having a psycho-stimulative effect; i.e., components which can be employed as the psycho-stimulative components of the psycho-stimulative composition will be described.

Piperitone (i.e., p-menth-1-en-3-one), which is a component of the psycho-controlling composition and has a psycho-stimulative effect, is known to have a mint-like aroma. In the present invention, either piperitone which has been isolated from an essential oil such as Japanese mint oil or *Eucalyptus* oil and purified through a routine method or a commercial piperitone product can be employed.

Isoamyl angelate (i.e., isoamyl(Z)-2-methyl-2-butenoate) is known to have a Roman chamomile-like, damascone-like rose-floral aroma. In the present invention, either isoamyl angelate which has been produced through a routine method or a commercial isoamyl angelate product can be employed.

Phenylethyl angelate (2-phenylethyl angelate: i.e., 2-phenylethyl(Z)-2-methyl-2-butenoate) is known to have an orris-type, fresh rose petal-like aroma. In the present invention, either phenylethyl angelate which has been produced through a routine method or a commercial phenylethyl angelate product can be employed.

Cuminyl alcohol (i.e., 4-isopropylbenzyl alcohol) is known to have a moderate oily, spicy, and floral aroma. In the present invention, either cuminyl alcohol which has been isolated from an essential oil such as cumin oil and purified through a routine method or a commercial cuminyl alcohol product can be employed.

Menthalactone (i.e., 3,6-dimethyl-5,6,7,7a-tetrahydro-2 (4H)-benzofuranone) is known to have a sweet, coumarin-like, and coconut-like aroma. In the present invention, either menthalactone which has been isolated from an essential oil such as mint oil and purified through a routine method or a commercial menthalactone product can be employed.

Ethyl myristate (i.e., ethyl tetradecanoate) is known to have a sweet orris-like waxy aroma. In the present invention, either ethyl myristate which has been isolated from an essential oil such as apricot oil and purified through a routine method or a commercial ethyl myristate product can be employed.

Perilla aldehyde (i.e., dihydrocuminyl aldehyde) is known to have a perilla-like, cumin-like medicinal herb-type aroma. In the present invention, either perilla aldehyde which has been isolated from an essential oil such as perilla oil and purified through a routine method or a commercial perilla aldehyde product can be employed.

When the psycho-controlling composition contains at least perilla aldehyde (having psycho-stimulative effect) as an effective component, the composition preferably contains in combination perilla alcohol as an additional component, from the viewpoint of enhancement of psycho-stimulative effect. Perilla alcohol, also called dihydrocuminyl alcohol, is known to have a herbal, woody, and oil-like floral aroma. In the present invention, either perilla alcohol which has been isolated from an essential oil such as perilla oil and purified through a routine method or a commercial perilla alcohol product can be employed.

Thus, when perilla aldehyde and perilla alcohol are used in combination in the psycho-controlling composition, particularly as the effective components of the psycho-stimulative composition, a synergistic psycho-stimulative effect can be provided.

The psycho-controlling composition of the present invention may be a perfume composition which is exclusively composed of, as essential components, one or more components selected from the group consisting of terpinyl butyrate, γ-nonalactone, acetyl isoeugenol, methyl anisate, terpineol, nerol, chrysanthenone, lyral, lilial, β-phenylethyl alcohol, γ-methyl ionone, Iso E Super, Z-3-hexenyl salicylate, p-methylphenylacetaldehyde, limonene, ocimene, helional, linalyl acetate, geranyl acetate, geraniol, hedione, linalool, citronellol, and γ-hexalactone and/or one or more components selected from the group consisting of piperitone, isoamyl angelate, phenylethyl angelate, cuminyl alcohol, menthalactone, ethyl myristate, and perilla aldehyde (when at least perilla aldehyde is selected as one of the above components, the composition may contain perilla alcohol as an additional component). Alternatively, the composition may further contain another perfume component, an essential oil, or a similar component for, for example, satisfying the user's fragrance taste within an appropriate amount range so as not to cancel out a desired psycho-controlling effect by other effects, such as a harmonizing effect and a masking effect. The psycho-controlling composition can be generally employed as a compounded perfume. Other components which can be generally added to perfume compositions; e.g., an antioxidant, a preservative, a chelating agent, a UV-absorber, and a colorant, can also be incorporated into the psycho-controlling composition.

The psycho-sedative composition of the present invention may be a perfume composition which is exclusively composed of, as essential components, one or more components selected from the group consisting of terpinyl butyrate, γ-nonalactone, acetyl isoeugenol, methyl anisate, terpineol, nerol, chrysanthenone, lyral, lilial, β-phenylethyl alcohol, γ-methyl ionone, Iso E Super, Z-3-hexenyl salicylate, p-methylphenylacetaldehyde, limonene, ocimene, helional, linalyl acetate, geranyl acetate, geraniol, hedione, linalool, citronellol, and γ-hexalactone. Alternatively, the composition may further contain another perfume component, an essential oil, or a similar component for, for example, satisfying the user's fragrance taste within an appropriate amount range so as not to cancel out a desired psycho-sedative effect by other effects such as a harmonizing effect and a masking effect. The psycho-sedative composition can be generally employed as a compounded perfume. Other components which can be generally added to perfume compositions; e.g., an antioxidant, a preservative, a chelating agent, a UV-absorber, and a colorant, can also be incorporated into the psycho-sedative composition.

The psycho-stimulative composition of the present invention may be a perfume composition which is exclusively composed of, as essential components, one or more components selected from the group consisting of piperitone, isoamyl angelate, phenylethyl angelate, cuminyl alcohol, menthalactone, ethyl myristate, and perilla aldehyde (when at least perilla aldehyde is selected as one of the above components, the composition may contain perilla alcohol as an additional component). Alternatively, the composition may further contain another perfume component and an essential oil for satisfying the user's fragrance taste within an appropriate amount range so as not to cancel out a desired psycho-stimulative effect by other effects such as a harmonizing effect and a masking effect. The psycho-stimulative composition can be generally employed as a compounded perfume. Other components which can be generally added to perfume compositions; e.g., an antioxidant, a preservative, a chelating agent, a UV-absorber, and a colorant, can also be incorporated into the psycho-stimulative composition.

The psycho-controlling composition (encompassing the psycho-sedative composition and the psycho-stimulative composition) is generally employed as a compounded perfume and can exert a psycho-controlling effect (including a psycho-sedative effect and a psycho-stimulative effect) when the composition is incorporated into an object which allows incorporation of the perfume.

No particular limitation is imposed on the object, and examples thereof include external compositions such as cosmetics; daily-use goods such as room deodorants, room aromatic products, and aroma candles; and food compositions.

The amount of the psycho-controlling composition (encompassing the psycho-sedative composition and the psycho-stimulative composition) which is to be added to the aforementioned object can be arbitrarily adjusted in accordance with factors such as the type of the object and the type of perfume, within an appropriate range so long as the psycho-controlling effect (including the psycho-sedative effect and the psycho-stimulative effect) can be provided. The amount can be generally predetermined in accordance with the amount of a compounded perfume generally employed. In many cases, the amount of the composition is preferably 0.01 to 50.0 mass % based on the object, more preferably 0.1 to 20.0 mass %, further preferably 1.0 to 10.0 mass %.

When the psycho-sedative composition is incorporated into an object, the total amount of psycho-sedative components (one or more species selected from the group consisting of terpinyl butyrate, γ-nonalactone, acetyl isoeugenol, methyl anisate, terpineol, nerol, chrysanthenone, lyral, lilial, β-phenylethyl alcohol, γ-methyl ionone, Iso E Super, Z-3-hexenyl salicylate, p-methylphenylacetaldehyde, limonene, ocimene, helional, linalyl acetate, geranyl acetate, geraniol, hedione, linalool, citronellol, and γ-hexalactone) is, in many cases, preferably 0.001 to 50.0 mass % based on the object, more preferably 0.01 to 20.0 mass %, from the viewpoint of the user's taste, further preferably 1.0 to 10.0 mass %. When the total amount of the components is less than 0.001 mass % based on the object, failure to attain a sufficient psycho-sedative effect tends to occur even when the effects of other components are minimized. When the total amount is in excess of 50.0 mass %, enhancement of the psycho-sedative effect commensurate with the total amount of the psycho-sedative components fails to be attained, generally resulting in poor aroma balance.

When the psycho-stimulative composition is incorporated into an object, the total amount of psycho-stimulative components (one or more species selected from the group consisting of piperitone, isoamyl angelate, phenylethyl angelate, cuminyl alcohol, menthalactone, ethyl myristate, and perilla aldehyde) is, in many cases, preferably 0.0005 to 50.0 mass % based on the object, more preferably 0.01 to 20.0 mass %, from the viewpoint of the user's taste, further preferably 1.0 to 10.0 mass %. When the total amount of the components is less than 0.0005 mass % based on the object, failure to attain a sufficient psycho-stimulative effect tends to occur even when the effects of other components are minimized. When the total amount is in excess of 50.0 mass %, enhancement of the psycho-stimulative effect commensurate with the total amount of the psycho-stimulative components fails to be attained, generally resulting in poor aroma balance.

As mentioned above, when perilla aldehyde is selected as one of the effective components, the composition preferably contains perilla alcohol in combination. In this case, the amount of perilla alcohol incorporated into the composition is preferably 0.0005 to 50.0 mass % based on the object, more preferably 0.01 to 20.0 mass %, further preferably 1.0 to 10.0 mass %.

The object to which the psycho-controlling composition is added can contain, in addition to the psycho-controlling composition, constituents which are generally employed in the object and selected in accordance with the type of the object, within a range so long as the target effect of the present invention is not impaired.

For example, when the object is an external composition such as a cosmetic, components which are generally employed in the external composition and selected in accordance with the specific form of the external composition (e.g., liquid, powder, granules, aerosol, solid, or gel) or the product form can be incorporated into the object in addition to the psycho-controlling composition of the present invention.

Specific examples of the product form of cosmetics, which are most preferred embodiments of the external composition, include perfume products, eau de toilette, eau de Cologne, creams and milky lotions, lotions, foundations, face powders, lipsticks, pomades, soaps, shampoos and rinses, body shampoos, body rinses, body powders, and bath preparations.

Specific examples of the product form of daily daily-use goods include room aromatic products, room deodorants, and aroma candles.

The present invention also provides a psycho-controlling method comprising allowing the psycho-controlling composition to be inhaled for mental control.

The subject to which the psycho-controlling composition is inhaled is generally human, but mammals such as dogs and cats may also be the subjects. Generally, inhalation of the composition is performed by the mediation of an object (external compositions, daily-use goods, food compositions, etc.) containing the psycho-controlling composition of the present invention. When the inhalation subject inhales the psycho-controlling composition contained in an object by way of a general mode of employment of the object or a designated mode thereof (exodermal application of external compositions such as cosmetics, burning an aroma candle (daily-use goods), placing or spraying aromatic products or deodorants in a room, ingesting food compositions, etc.), mental control of the subject can be attained by psycho-controlling components contained in the psycho-controlling composition.

No limitation is imposed on the type of mental control; i.e., the psycho-controlling method may be a psycho-sedating method or a psycho-stimulating method.

Thus, the present invention provides a psycho-sedating method comprising allowing the psycho-sedative composition to be inhaled for mental sedation and a psycho-stimulating method comprising allowing the psycho-stimulative composition to be inhaled for mental stimulation.

EXAMPLES

The present invention will next be described in more detail by way of examples. The amount of a substance represented by "%" refers to the mass % of the substance with respect to the entirety of the object into which the substance has been incorporated.

CNV Test

The psycho-sedative effect was investigated by measuring negative changes in electric potential, so-called contingent negative variation (CNV). CNV is known to be a slow cerebral potential variation which relates to psychological processes such as alertness, expectation, and anticipation and to changes in the level of consciousness.

In order to screen out a compound having a psycho-sedative or psycho-stimulative effect, a light signal which indicates start of movement is emitted two seconds after stimulation with a warning sound, and a panelist is required to react (i.e., push a button) simultaneously with the recognition of the light. During repetition of a series of such processes, an aromatic product sample is arranged about 10 cm under the nose of the panelist so that its scent can be acknowledged with breathing. An electrode for the measurement of CNV is set on the forehead of the panelist so as to record electric potential between the forehead and an earlobe. It has already been reported that the CNV amplitude increases when caffeine having an arousal effect is perorally administered to humans, whereas the amplitude decreases when nitrazepam having a sedative effect is allowed to be inhaled.

Such variation in CNV amplitude occurs significantly during an initial interval of 400 to 1,000 msec after the sound stimulation, and the corresponding CNV amplitude variation area is expressed by percentage (%) based on a blank (odorless stimulation) which is taken as 100%. In this test, the psycho-sedative effect was evaluated by use of the percentage as an index. A relative area of 100% or less indicates a sedative effect, and a relative area of 100% or more indicates an arousal effect.

Test Example (1) Psycho-Sedative Effect

The following samples were prepared: a 1% ethanol solution of each of terpinyl butyrate, γ-nonalactone, acetyl isoeugenol, methyl anisate, terpineol, nerol, chrysanthenone, lyral, lilial, β-phenylethyl alcohol, γ-methyl ionone, Iso E Super, Z-3-hexenyl salicylate, p-methylphenylacetaldehyde, limonene, ocimene, helional, linalyl acetate, geranyl acetate, geraniol, hedione, linalool, citronellol, and γ-hexalactone (all compounds were commercial products); a 1% ethanol solution of 3-dimethoxy-5-methylbenzene (hereinafter may be referred to as DMMB) (commercial product) whose sedative effect is reported in, for example, Japanese Patent Application Laid-Open (kokai) No. 6-172781; and a 1% ethanol solution of lemon oil (commercial product), which according to folklore has been acknowledged to have a psycho-stimulative effect. Five healthy female panelists were subjected to the aforementioned CNV test.

The results are shown in FIG. 1. As is clear from FIG. 1, terpinyl butyrate, γ-nonalactone, acetyl isoeugenol, methyl anisate, terpineol, nerol, chrysanthenone, lyral, lilial, β-phenylethyl alcohol, γ-methyl ionone, Iso E Super, Z-3-hexenyl salicylate, p-methylphenylacetaldehyde, limonene, ocimene, helional, linalyl acetate, geranyl acetate, geraniol, hedione, linalool, citronellol, and γ-hexalactone are acknowledged to have a psycho-sedative effect similar to that of DMMB (psycho-stimulative effect of lemon oil was confirmed).

(2) Psycho-Stimulative Effect (A) The following samples were prepared: a 1% ethanol solution of each of piperitone, isoamyl angelate, cuminyl alcohol, menthalactone, ethyl myristate, and phenylethyl angelate (all compounds were commercial products); a 1% ethanol solution of 3-dimethoxy-5-methylbenzene (hereinafter may be referred to as DMMB) (commercial product) whose sedative effect is reported in, for example, Japanese Patent Application Laid-Open (kokai) No. 6-172781; and a 1% ethanol solution of lemon oil (commercial product), which according to folklore has been acknowledged to have a psycho-stimulative effect. Five healthy female adult panelists were subjected to the aforementioned CNV test.

Figure 2:
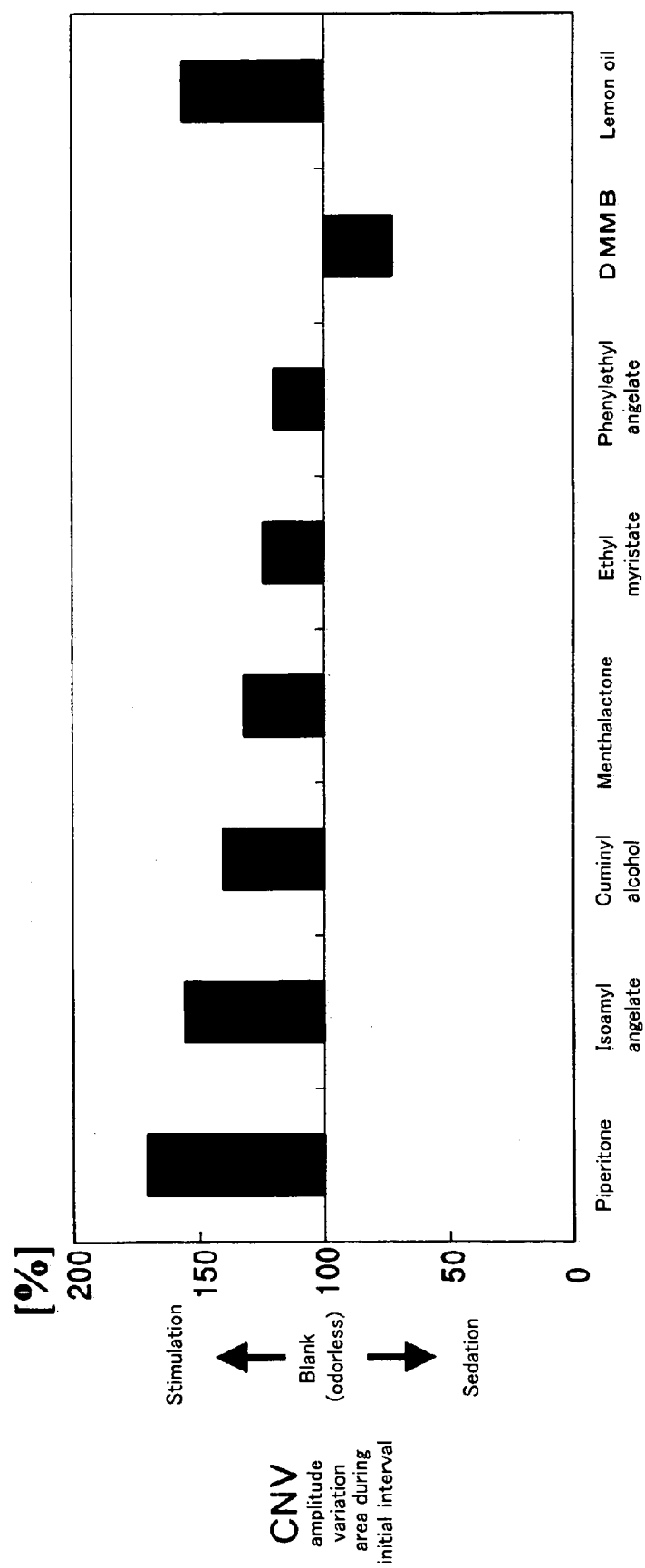
FIG. 2 is a graph showing measured CNV values of components contained in the psycho-controlling composition which can be employed as the psycho-stimulative composition (i.e., piperitone, isoamyl angelate, cuminyl alcohol, menthalactone, ethyl myristate, and phenylethyl angelate).

The results are shown in FIG. 2. As is clear from FIG. 2, piperitone, isoamyl angelate, cuminyl alcohol, menthalactone, ethyl myristate, and phenylethyl angelate are acknowledged to have a psycho-stimulative effect similar to that of limone oil (psycho-sedative effect of DMMB was confirmed).

(B) The following samples were prepared: a 1% ethanol solution of perilla aldehyde (commercial product); a 1% ethanol solution of perilla alcohol (commercial product); a 1% ethanol solution of DMMB (commercial product); and a 1% ethanol solution of lemon oil (commercial product). Five healthy female adult panelists were subjected to the aforementioned CNV test.

Figure 3:
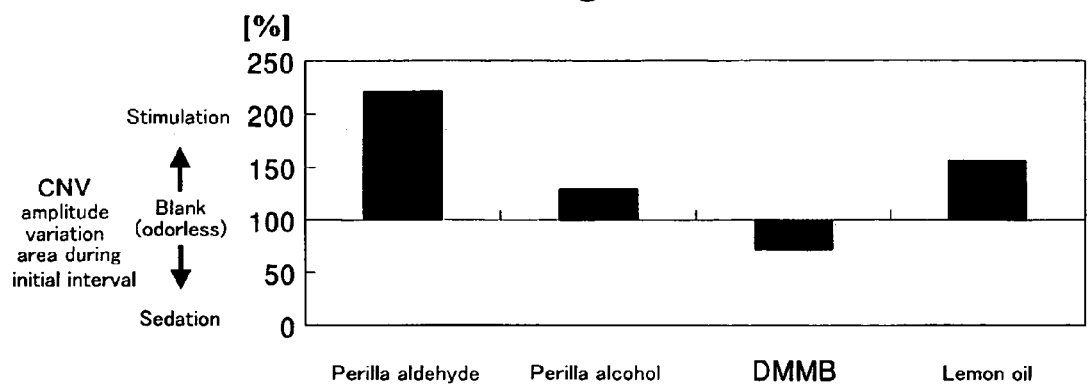
FIG. 3 is a graph showing measured CNV values of components including perilla aldehyde contained in the psycho-controlling composition which can be employed as the psycho-stimulative composition.

The results are shown in FIG. 3. As is clear from FIG. 3, perilla aldehyde and perilla alcohol are acknowledged to have a psycho-stimulative effect. In particular, perilla aldehyde exhibited a remarkably strong psycho-stimulative effect as compared with lemon oil.

(C) Synergistic Psycho-Stimulative Effect

The following samples were prepared: a 0.05% ethanol solution of solo perilla aldehyde (1); a 0.05% ethanol solution of solo perilla alcohol (2); and an ethanol solution containing perilla aldehyde (0.05%) and perilla alcohol (0.05%) (3). Five healthy female adult panelists were subjected to the aforementioned CNV test.

Figure 4:
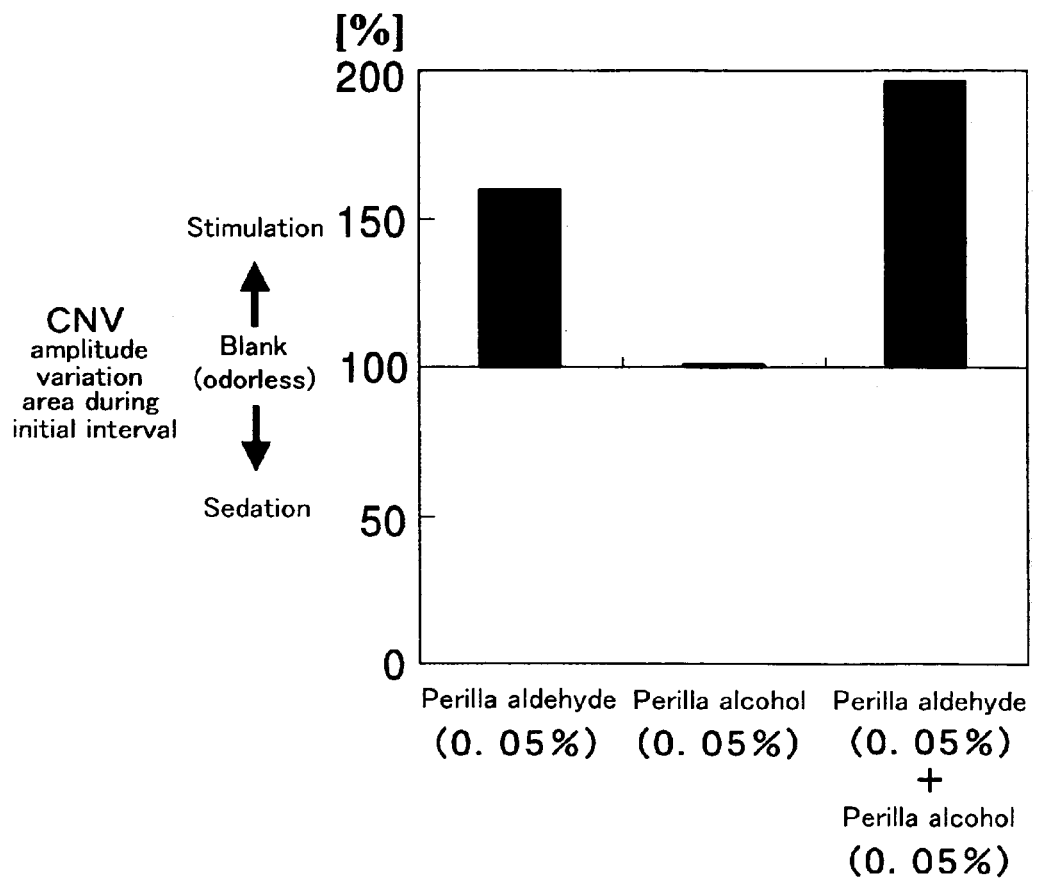
FIG. 4 is a graph showing investigation results of a synergistic psycho-stimulative effect provided by perilla aldehyde and perilla alcohol.

The results are shown in FIG. 4. As shown in FIG. 4, the solution containing solo perilla aldehyde (1) is acknowledged to have a psycho-stimulative effect, whereas the solution containing solo perilla alcohol (2) is acknowledged to have only a slight psycho-stimulative effect. However, in the case of the mixture solution of perilla aldehyde and perilla alcohol in combination (3), the psycho-stimulative effect was remarkably enhanced. Thus, use of perilla aldehyde and perilla alcohol in combination is acknowledged to synergistically enhance the psycho-stimulative effect.

Specific formulations of the psycho-controlling composition of the present invention will be shown in the following Examples. The psycho-controlling compositions of Examples 1 to 9 to be employed as the psycho-sedative composition were acknowledged to have a psycho-sedative effect by the aforementioned CNV test, and the psycho-controlling compositions of Examples 10 to 17 to be employed as the psycho-stimulative composition were acknowledged to have a psycho-stimulative effect by the aforementioned CNV test.

Example 1

Psyco-Sedative Perfume Composition

| Formulation | Amount (parts by mass) |
| --- | --- |
| γ-Nonalactone | 0.2 |
| Methyl anisate | 2.0 |
| p-Methylphenylacetaldehyde | 2.0 |
| Ocimene (1%) | 0.5 |
| γ-Hexalactone | 1.0 |
| Bergamot oil | 10.0 |
| Methyl dihydro jasmonate (Hedione) | 20.0 |
| Linalool | 28.0 |
| Orange oil | 1.0 |
| Linalool oxide | 5.0 |
| Phenylethyl alcohol | 5.0 |
| Benzyl alcohol | 1.0 |
| Benzaldehyde | 1.0 |
| Indol (10%) | 0.5 |
| Abs. Cassis | 2.0 |
| Nerol | 2.0 |
| Abs. Jasmin | 1.0 |
| Iso E super | 5.0 |
| Galaxolide (50%) | 10.0 |
| Bacdanol | 1.0 |
| Anis alcohol | 1.0 |
| DPG | 0.8 |

Example 2

Psyco-Sedative Perfume Composition

| Formulation | Amount (parts by mass) |
| --- | --- |
| Terpinyl butylate | 1.0 |
| γ-Nonalactone | 0.1 |
| Ocimen (1%) | 0.5 |
| Methyl dihydro jasmonate (Hedione) | 20.0 |
| Vertofix coeur | 15.0 |
| Polysantol | 10.0 |
| Galaxolide (50%) | 10.0 |
| Bergamot oil | 9.0 |
| Orange oil | 4.0 |
| Ethyllinalool | 3.0 |
| Lilial | 2.0 |
| Bacdanol | 1.0 |
| Linalool | 1.0 |
| Coumarin | 1.0 |
| Ambroxane | 1.0 |
| Citronellol | 1.0 |
| β-Phenylethyl alcohol | 1.0 |
| Calone (1%) | 1.0 |
| Pine oil | 1.0 |
| Benzyl acetate | 0.5 |
| Stemone | 0.5 |
| Terpineol | 2.0 |
| Damascone alpha (10%) | 0.3 |
| Allylamyl glycolate | 0.2 |
| Evernyl | 0.2 |
| Triplal | 0.2 |
| DPG | 13.5 |

Example 3

Psyco-Sedative Perfume Composition

| Formulation | Amount (parts by mass) |
| --- | --- |
| Terpinyl butylate | 1.0 |
| γ-Nonalactone | 0.2 |
| Methyl anisate | 1.0 |
| Chrysantenone | 0.5 |
| p-Methylphenylacetaldehyde | 2.0 |
| Hexalactone gannma | 1.0 |
| Methyl dihydro jasumonate (Hedion) | 15.0 |
| Lyral | 13.0 |
| Iso E super | 12.0 |
| Galaxolide (50%) | 10.0 |
| Orange oil | 5.0 |
| Linalool | 15.0 |
| γ-Methyl ionone | 5.0 |
| Limonene | 10.0 |
| cis-3-Hexenyl salicylate | 2.0 |
| β-Naphthylmethyl ether | 1.0 |
| Santalex | 1.0 |
| Mandarine oil | 1.0 |
| Rose oil | 0.5 |
| Laurel leaf oil | 0.5 |
| Allylamyl glycolate | 0.3 |
| Damacenone | 0.2 |
| DPG | 2.8 |

Example 4

Psyco-Sedative Perfume Composition

| Formulation | Amount (parts by mass) |
| --- | --- |
| Terpinyl butylate | 1.0 |
| γ-Nonalactone | 0.2 |
| Methyl anisate | 1.0 |
| p-Methylphenylacetaldehyde | 2.0 |
| γ-Hexalactone | 0.5 |
| β-Phenylethyl alcohol | 10.0 |
| Limonene | 10.0 |
| Methyl dihydro jasmonate (Hedione) | 10.0 |
| Lyral | 10.0 |
| β-Ionone | 7.0 |
| Geranyl acetate | 1.0 |
| Citronellol | 7.0 |
| Geraniol | 2.0 |
| Bergamot oil | 5.0 |
| Linalool | 5.0 |
| Hexyl salicylate | 5.0 |
| Galaxolide (50%) | 5.0 |
| cis-3-Hexenyl salicylate | 5.0 |
| Benzyl acetate | 5.0 |
| Lime oil | 3.0 |
| Mandarin oil | 2.0 |
| Rose oil | 2.0 |
| Abs. Jasmin | 0.5 |
| cis-3-Hexenol | 0.2 |
| DPG | 0.6 |

Example 5

Psyco-Sedative Perfume Composition

| Formulation | Amount (parts by mass) |
| --- | --- |
| Acetyl iso Eugenol | 2.0 |
| Bacdanol | 2.5 |
| Bergamot oil | 5.0 |
| Grapefruit oil | 4.0 |
| Linalool | 3.0 |
| Linalyl acetate | 3.0 |
| Cedramber | 1.5 |
| Coumarin | 1.0 |
| Methyl dihydro jasmonate (Hedione) | 30.0 |
| Ambroxane | 0.5 |
| Cardamon oil | 0.5 |
| Geranium oil | 0.5 |
| Limonene | 3.0 |
| Allyl amyl glycolate | 0.1 |
| Helional | 1.0 |
| Damascenone (10%) | 0.2 |
| Cassis base 345B | 1.0 |
| Benzyl acetate | 1.0 |
| Iso E super | 20.0 |
| Habanolide | 8.0 |
| Musk T | 5.0 |
| Ethyl linalool | 5.0 |
| Lavandin oil | 2.0 |
| DPG | 0.2 |

Example 6

Psyco-Sedative Perfume Composition

| Formulation | Amount (parts by mass) |
| --- | --- |
| Acetyl iso Eugenol | 1.0 |
| Methyl dihydro jasmonate (Hedione) | 20.0 |
| Iso E super | 15.0 |
| Bergamot oil | 10.0 |
| DPG | 5.2 |
| Linalyl acetate | 5.0 |
| Habanolide | 5.0 |
| Dihydro myrcenol | 5.0 |
| Vertofix coeur | 5.0 |
| Bacadanol | 3.0 |
| Linalool | 3.0 |
| Musk T | 3.0 |
| Lavandin oil | 3.0 |
| Lyral | 3.0 |
| Coumarin | 2.0 |
| Limonene | 2.0 |
| Patchouli oil | 2.0 |
| Citronellol | 2.0 |
| β-Phenylethyl alcohol | 2.0 |
| Vetiver oil | 1.0 |
| Ambroxane | 0.5 |
| Damascenone (10%) | 0.5 |
| Benzyl acetate | 0.5 |
| Evernyl | 0.5 |
| Eugenol | 0.2 |
| Jasmin oil | 0.2 |
| Vanillin | 0.1 |
| Cinamon bark oil | 0.1 |
| Galbanum oil | 0.1 |
| Allylcyclohexyl propionate | 0.1 |

Example 7

Psyco-Sedative Perfume Composition

| Formulation | Amount (parts by mass) |
| --- | --- |
| Acetyl iso Eugenol | 5.0 |
| Methyl dihydro jasmonate (Hedione) | 15.0 |
| Lyral | 13.0 |
| Iso E super | 12.0 |
| Galaxolide (50%) | 10.0 |
| Orange oil | 5.0 |
| Linalool | 20.0 |
| γ-Methyl ionone | 5.0 |
| Limonene | 5.0 |
| cis-3-Hexenyl salicylate | 2.0 |
| β-Naphthylmethyl ether | 1.0 |
| Santalex | 1.0 |
| Mandarine oil | 1.0 |
| Rose oil | 0.5 |
| Laurel leaf oil | 0.5 |
| Allylamyl glycolate | 0.3 |
| Damascenone (10%) | 0.2 |
| DPG | 3.5 |

Example 8

Psyco-Sedative Perfume Composition

| Formulation | Amount (parts by mass) |
| --- | --- |
| Acetyl iso Eugenol | 2.0 |
| β-Phenylethyl alcohol | 12.0 |
| Limonene | 10.0 |
| Methyl dihydro jasmonate (Hedione) | 10.0 |
| Lyral | 10.0 |
| β-Ionone | 7.0 |
| Citronellol | 7.0 |
| Geraniol | 3.0 |
| Bergamot oil | 5.0 |
| Linalool | 5.0 |
| cis-3-Hexenyl salicylate | 5.0 |
| Benzyl acetate | 5.0 |
| Lime oil | 3.0 |
| Mandarine oil | 2.0 |
| Rose oil | 2.0 |
| Abs. Jasmin | 0.5 |
| cis-3-Hexenol | 0.2 |
| DPG | 1.3 |

Example 9

Psyco-Sedative Perfume Composition

| Formulation | Amount (parts by mass) |
| --- | --- |
| Limonene | 8.0 |
| Linalool | 10.0 |
| Linalyl acetate | 5.0 |
| Bergamot oil | 5.0 |
| Liffarome | 0.05 |
| Benzyl acetate | 5.0 |
| β-Phenylethyl alcohol | 8.0 |
| Lilial | 5.0 |
| Lyral | 3.0 |
| β-ionone | 0.5 |
| Methyl dihydro jasmonate (Hedione) | 15.0 |
| α-Hexyl cirmamic aldrhyde | 10.0 |
| p-Methylphenylacetaldehyde | 2.0 |
| Helional | 0.5 |
| Aldehyde C-14 | 0.1 |
| Iso E Super | 5.0 |
| Galaxolide (50%) | 10.0 |
| Ethylene brassylate | 3.0 |
| Benzyl benzonate | 4.85 |

Example 10

Psyco-Stimulative Perfume Composition

| Formulation | Amount (parts by mass) |
| --- | --- |
| Isoamyl angelate | 0.5 |
| Cuminyl alcohol | 2.0 |
| Menthalactone | 0.5 |
| 2-Phenyl ethyl angelate | 0.2 |
| Methyl jasmonate | 20.0 |
| Vertofix | 20.0 |
| Galaxolide (50%) | 8.0 |
| Bergamot oil | 10.0 |
| Lemon oil | 5.0 |
| Ethyl linalool | 5.0 |
| Musk T | 5.0 |
| Dihydro myrcenol | 5.0 |
| Myrcenyl acetate | 5.0 |
| Grapefruit oil | 5.0 |
| Orange oil | 3.0 |
| Phenyl propyl alcohol | 2.0 |
| DPG | 2.8 |
| Ambroxan | 1.0 |
| Benzyl acetate | 1.0 |
| Cassis base 345 B | 1.0 |
| Dimetol | 0.2 |
| Rosemary oil | 1.0 |
| Cashmerane | 0.5 |
| Bacdanol | 0.5 |
| Estragon oil | 0.3 |
| Allylanyl glycolate | 0.2 |
| cis-3-Hexenol | 0.2 |
| Jasmin oil | 0.1 |

Example 11

Psyco-Stimulative Perfume Composition

| Formulation | Amount (parts by mass) |
| --- | --- |
| Piperitone | 0.5 |
| Isoamyl angelate | 0.5 |
| Cuminyl alcohol | 2.0 |
| Menthalactone | 0.5 |
| 2-Phenylethyl angelate | 0.2 |
| Habanolide | 20.0 |
| Vertofix | 20.0 |
| Methyl jasmonate | 20.0 |
| Lemon oil | 10.0 |
| Dimetol | 1.0 |
| Laurel leaf oil | 5.0 |
| Hexyl cinnamic aldehyde | 3.0 |

-continued

| Formulation | Amount (parts by mass) |
|---|---|
| Sandalore | 2.0 |
| Ethyl linalool | 2.0 |
| Cashmerane | 1.0 |
| Cassis 345 B | 1.0 |
| Ambrettolide | 1.0 |
| Bay leaf oil | 0.5 |
| Stemone | 0.5 |
| Abs. Petitgrain bigarade | 0.2 |
| DPG | 9.1 |

Example 12

Psyco-Stimulative Perfume Composition

| Formulation | Amount (parts by mass) |
|---|---|
| Piperitone | 0.5 |
| Isoamyl angelate | 0.5 |
| Ethyl myristate | 0.2 |
| 2-Phenylethyl angelate | 0.2 |
| Lemon oil | 18.0 |
| Orange oil | 10.0 |
| Bergamot oil | 12.0 |
| Ethyl linalool | 10.0 |
| Myrcenyl acetate | 15.0 |
| Lime oil | 3.0 |
| Geranium oil | 1.5 |
| Galaxolide (50%) | 10.0 |
| Coumarin | 0.5 |
| Lavandin oil | 1.0 |
| Santalex | 2.0 |
| Verdox | 8.0 |
| β-Naphthylmethyl ether | 1.0 |
| DPG | 6.6 |

Example 13

Psyco-Stimulative Perfume Composition

| Formulation | Amount (parts by mass) |
|---|---|
| Cuminyl alcohol | 0.5 |
| Menthalactone | 0.5 |
| β-Phenylethyl alcohol | 12.0 |
| Lemon oil | 20.0 |
| Methyl jasmonate | 8.0 |
| Isopropyl cyclohexyl methanol | 8.0 |
| β-ionone | 7.0 |
| Dimetol | 1.5 |
| Bergamot oil | 5.0 |
| Ethyl linalool | 5.0 |
| Hexyl salicylate | 9.0 |
| Galaxolide (50%) | 4.0 |
| Benzyl acetate | 5.0 |
| Lime oil | 3.0 |
| Mandarin oil | 2.0 |
| Rose oil | 1.0 |
| Abs. Jasmin | 2.0 |
| cis-3-Hexenol | 0.2 |
| DPG | 6.3 |

Example 14

Psyco-Stimulative Perfume Composition

| Formulation | Amount (parts by mass) |
|---|---|
| Perilla aldehyde | 0.5 |
| Perilla alcohol | 1.0 |
| Methyl jasmonate | 20.0 |
| Lemon oil | 20.0 |
| Vertifix | 12.0 |
| Bergamot oil | 10.0 |
| Galaxolide (50%) | 10.0 |
| Orange oil | 7.0 |
| DPG | 5.2 |
| Ethyl linalool | 5.0 |
| Musk T | 3.0 |
| Dimethyl ethyl phenyl propanal | 2.0 |
| Isopropyl cyclohexyl methanol | 2.0 |
| Benzyl acetate | 1.0 |
| Damascone alpha (10%) | 0.5 |
| Allylamyl glycolate | 0.3 |
| Triplal | 0.2 |
| Ambroxan | 0.2 |
| Eugenol | 0.1 |

Example 15

Psyco-Stimulative Perfume Composition

| Formulation | Amount (parts by mass) |
|---|---|
| Perilla aldehyde | 0.3 |
| Perilla alcohol | 0.7 |
| Methyl jasmonate | 30.0 |
| Lemon oil | 10.0 |
| Vertofix | 10.0 |
| Galaxolide (50%) | 10.0 |
| Dihydro myrcenol | 10.0 |
| Vertofix coeur | 5.0 |
| Mandarine oil | 5.0 |
| Lavender oil | 5.0 |
| Ethyl linalool | 3.0 |
| DPG | 3.5 |
| Myrcenyl acetate | 2.0 |
| Dimetol | 0.5 |
| Coumarin | 1.0 |
| Hexyl salicylate | 1.0 |
| Benzyl acetate | 0.5 |
| Patchouli oil | 0.5 |
| Cassis base 345 B | 0.5 |
| Damascenone (10%) | 0.5 |
| Clove oil | 0.3 |
| Allylamyl glycolate | 0.2 |
| Black pepper oil | 0.2 |
| Jasmin oil | 0.2 |
| Ambroxan | 0.1 |

Example 16

Psyco-Stimulative Perfume Composition

| Formulation | Amount (parts by mass) |
| --- | --- |
| Perilla aldehyde | 0.3 |
| Perilla alcohol | 0.7 |
| Lemon oil | 18.0 |
| Orange oil | 10.0 |
| Bergamot oil | 12.0 |
| Ethyl linalool | 10.0 |
| Myrcenyl acetate | 15.0 |
| Lime oil | 3.0 |
| Geranium oil | 1.5 |
| Galaxolide (50%) | 10.0 |
| Coumarin | 0.5 |
| Lavandin oil | 1.0 |
| Santalex | 2.0 |
| Verdox | 8.0 |
| β-Naphthylmethyl ether | 1.0 |
| DPG | 7.0 |

Example 17

Psyco-Stimulative Perfume Composition

| Formulation | Amount (parts by mass) |
| --- | --- |
| Perilla aldehyde | 0.2 |
| Perilla alcohol | 0.5 |
| β-Phenylethyl alcohol | 12.0 |
| Lemon oil | 20.0 |
| Methyl jasmonate | 8.0 |
| Isopropyl cyclohexyl methanol | 8.0 |
| β-ionone | 7.0 |
| Dimetol | 1.0 |
| Bergamot oil | 5.0 |
| Ethyl linalool | 5.0 |
| Hexyl salicylate | 10.0 |
| Galaxolide (50%) | 5.0 |
| Benzyl acetate | 5.0 |
| Lime oil | 3.0 |
| Mandarin oil | 2.0 |
| Rose oil | 1.0 |
| Abs. Jasmin | 2.0 |
| cis-3-Hexenol | 0.2 |
| DPG | 5.1 |

Typical product formulation examples of external compositions and daily-use goods containing the psycho-controlling composition are described in the following Examples. External compositions or daily-use goods of Examples 18 to 31 and 45 which contain the psycho-controlling compositions had a psycho-sedative effect acknowledged by the sensory test carried out in a typical mode of employment of the product, and external compositions or daily-use goods of Examples 32 to 44 which contain the psycho-controlling compositions had a psycho-stimulative effect acknowledged by the sensory test carried out in a typical mode of employment of the product.

Example 18

Bath Preparation

| Formulation | Amount (parts by mass) |
| --- | --- |
| Sodium hydrogencarbonate | 70.0 |
| Sodium sulfate anhydrate | 28.8 |
| The psycho-sedative perfume composition of Example 3 | 1.0 |
| Pigment Y-202-1 | 0.2 |

<Production Method>

The above ingredients except for the psycho-sedative perfume composition were stirred by means of a V-type mixer so as to form a uniform mixture, and the psycho-sedative perfume composition was added thereto. The resultant mixture was further stirred thoroughly, to thereby form a uniform mixture serving as a bath preparation.

Example 19

Gel-Type Aromatic Product

| Formulation | Amount (parts by mass) |
| --- | --- |
| Carrageenan | 3.0 |
| Propylene glycol | 2.0 |
| Propylparaben | 0.3 |
| The psycho-sedative perfume composition of Example 3 | 5.0 |
| Ion-exchange water | 89.7 |

<Production Method>

Carrageenan, propylene glycol, and propylparaben were mixed together under stirring while ion-exchange water was added to the mixture. Subsequently, the resultant mixture was heated to about 80° C. under gentle stirring. After the temperature of the mixture had been lowered to about 65° C., the psycho-sedative perfume composition was added thereto under stirring by means of a homogenizer (3,000 rpm) so as to form a uniform phase. The product was poured into a predetermined container and was allowed to stand for cooling, to thereby produce a gel-type aromatic product.

Example 20

Liquid-Type Aromatic Product

| Formulation | Amount (parts by mass) |
| --- | --- |
| 95% Ethanol | 25.0 |
| Surfactant | 5.0 |
| The psycho-sedative perfume composition of Example 3 | 3.0 |
| Ion-exchange water | 67.0 |

<Production Method>

The above ingredients except for ion-exchange water were mixed together, and ion-exchange water was added thereto under gentle stirring, to thereby form a uniform mixture serving as a liquid-type aromatic product. In the production, polyoxyethylene nonylphenyl ether (EO-13) was employed as a surfactant.

Example 21

Liquid-Type Deodorant

| Formulation | Amount (parts by mass) |
| --- | --- |
| Deodorant source liquid FS-500M (product of Shiraimatsu Pharmaceutical Co., Ltd.) | 5.0 |
| 95% Ethanol | 10.0 |
| Surfactant | 10.0 |
| The psycho-sedative perfume composition of Example 2 | 10.0 |
| Ion-exchange water | 65.0 |

<Production Method>

The above ingredients except for ion-exchange water were mixed together, and ion-exchange water was added thereto under gentle stirring, to thereby produce a deodorant (liquid type). In the production, polyoxyethylene nonylphenyl ether (EO-10) was employed as a surfactant.

Example 22

Aerosol-Type Deodorant

| Formulation | Amount (parts by mass) |
| --- | --- |
| Deodorant source liquid FS-500M | 5.0 |
| 95% Ethanol | 20.0 |
| The psycho-sedative perfume composition of Example 2 | 10.0 |
| Ion-exchange water | 40.0 |
| Liquefied petroleum gas (4 kg/cm$^2$, 20° C.) | 25.0 |

<Production Method>

The above ingredients except for liquified petroleum gas were mixed together under stirring so as to form a uniform mixture, and a predetermined amount of the mixture was placed in an aerosol container. Subsequently, liquified petroleum gas was injected into the aerosol container equipped with a valve, to thereby produce a deodorant (aerosol type).

Example 23

Bath Preparation

| Formulation | Amount (parts by mass) |
| --- | --- |
| Sodium hydrogencarbonate | 70.0 |
| Sodium sulfate anhydrate | 28.8 |
| The psycho-sedative perfume composition of Example 7 | 1.0 |
| Pigment Y-202-1 | 0.2 |

<Production Method>

The above ingredients except for the psycho-sedative perfume composition were stirred by means of a V-type mixer so as to form a uniform mixture, and the psycho-sedative perfume composition was added thereto. The resultant mixture was further stirred thoroughly, to thereby form a uniform mixture serving as a bath preparation.

Example 24

Gel-Type Aromatic Product

| Formulation | Amount (parts by mass) |
| --- | --- |
| Carrageenan | 3.0 |
| Propylene glycol | 2.0 |
| Propylparaben | 0.3 |
| The psycho-sedative perfume composition of Example 7 | 5.0 |
| Ion-exchange water | 89.7 |

<Production Method>

Carrageenan, propylene glycol, and propylparaben were mixed together under stirring while ion-exchange water was added to the mixture. Subsequently, the resultant mixture was heated to about 80° C. under gentle stirring. After the temperature of the mixture had been lowered to about 65° C., the psycho-sedative perfume composition was added thereto under stirring by means of a homogenizer (3,000 rpm) so as to form a uniform phase. The product was poured into a predetermined container and was allowed to stand for cooling, to thereby produce a gel-type aromatic product.

Example 25

| Formulation | Amount (parts by mass) |
| --- | --- |
| 95% Ethanol | 25.0 |
| Surfactant | 5.0 |
| The psycho-sedative perfume composition of Example 7 | 3.0 |
| Ion-exchange water | 67.0 |

<Production Method>

The above ingredients except for ion-exchange water were mixed together, and ion-exchange water was added thereto under gentle stirring, to thereby form a uniform mixture serving as a liquid-type aromatic product. In the production, polyoxyethylene nonylphenyl ether (EO-13) was employed as a surfactant.

Example 26

Liquid-Type Deodorant

| Formulation | Amount (parts by mass) |
| --- | --- |
| Deodorant source liquid FS-500M (product of Shiraimatsu Pharmaceutical Co., Ltd.) | 5.0 |

-continued

| Formulation | Amount (parts by mass) |
| --- | --- |
| 95% Ethanol | 10.0 |
| Surfactant | 10.0 |
| Acetyl isoeugenol | 10.0 |
| Ion-exchange water | 65.0 |

<Production Method>

The above ingredients except for ion-exchange water were mixed together, and ion-exchange water was added thereto under gentle stirring, to thereby produce a deodorant (liquid type). In the production, polyoxyethylene nonylphenyl ether (EO-10) was employed as a surfactant.

Example 27

Aerosol-Type Deodorant

| Formulation | Amount (parts by mass) |
| --- | --- |
| Deodorant source liquid FS-500M | 5.0 |
| 95% Ethanol | 20.0 |
| Acetyl isoeugenol | 10.0 |
| Ion-exchange water | 40.0 |
| Liquefied petroleum gas (4 kg/cm$^2$, 20° C.) | 25.0 |

<Production Method>

The above ingredients except for liquified petroleum gas were mixed together under stirring so as to form a uniform mixture, and a predetermined amount of the mixture was placed in an aerosol container. Subsequently, liquified petroleum gas was injected into the aerosol container equipped with a valve, to thereby produce a deodorant (aerosol type).

Example 28

Cream

| Formulation | Amount (mass %) |
| --- | --- |
| Stearic acid | 10.0 |
| Stearyl alcohol | 4.0 |
| Butyl stearate | 8.0 |
| Glyceryl monostearate | 2.0 |
| Vitamin E acetate | 0.5 |
| Vitamin A palmitate | 0.1 |
| Macadamia nut oil | 1.0 |
| Tea seed oil | 3.0 |
| Glycerin | 4.0 |
| 1,2-Pentanediol | 3.0 |
| Sodium hyaluronate | 1.0 |
| Potassium hydroxide | 2.0 |
| Magnesium ascorbyl phosphate | 0.1 |
| L-Arginine hydrochloride | 0.01 |
| Trisodium edetate | 0.05 |
| The psycho-sedative perfume composition of Example 9 | 0.4 |
| Preservative | Suitable amount |
| Purified water | Balance |

<Production Method>

The cream was produced through a routine method.

Example 29

Cream

| Formulation | Amount (mass %) |
| --- | --- |
| Cetanol | 4.0 |
| Vaseline | 7.0 |
| Isopropyl myristate | 8.0 |
| Squalane | 15.0 |
| Glyceryl monostearate | 2.2 |
| POE(20) sorbitan monostearate | 2.8 |
| Vitamin E nicotinate | 2.0 |
| Glycerin | 10.0 |
| Sodium hyaluronate | 0.02 |
| Dipropylene glycol | 4.0 |
| Sodium pyrrolidonecarboxylate | 1.0 |
| The psycho-sedative perfume composition of Example 9 | 0.3 |
| Disodium edetate | 0.01 |
| Antioxidant | Suitable amount |
| Preservative | Suitable amount |
| Purified water | Balance |

<Production Method>

The cream was produced through a routine method.

Example 30

Milky Lotion

| Formulation | Amount (mass %) |
| --- | --- |
| Squalane | 5.0 |
| Oleyl oleate | 3.0 |
| Vaseline | 2.0 |
| Sorbitan sesquioleate | 0.8 |
| POE(20) oleyl ether | 1.2 |
| Evening primrose oil | 0.5 |
| 1,3-Butylene glycol | 4.5 |
| Ethanol | 3.0 |
| Carboxyvinyl polymer | 0.2 |
| Potassium hydroxide | 0.1 |
| L-Arginine L-aspartate | 0.01 |
| Salt of Edetic acid | 0.05 |
| The psycho-sedative perfume composition of Example 8 | 0.3 |
| Preservative | Suitable amount |
| Purified water | Balance |

<Production Method>

The milky lotion was produced through a routine method.

Example 31

Lotion

| Formulation | Amount (mass %) |
| --- | --- |
| Cetanol | 3.5 |
| POE oleyl alcohol ether | 2.0 |

-continued

| Formulation | Amount (mass %) |
| --- | --- |
| 2-Ethylhexyl p-dimethylaminobenzoate | 0.18 |
| 1,3-Butylene glycol | 9.5 |
| Sodium pyrrolidonecarboxylate | 0.5 |
| Nicotinamide | 0.3 |
| Glycerin | 5.0 |
| Syringaaldehyde (p-methylphenylacetaldehyde) | 0.05 |
| Purified water | Balance |

<Production Method>

The lotion was produced through a routine method.

Example 32

Bath Preparation

| Formulation | Amount (parts by mass) |
| --- | --- |
| Sodium hydrogencarbonate | 70.0 |
| Sodium sulfate anhydrate | 28.8 |
| The psycho-stimulative perfume composition of Example 12 | 1.0 |
| Pigment Y-202-1 | 0.2 |

<Production Method>

The above ingredients except for the perfume composition were stirred by means of a V-type mixer so as to form a uniform mixture, and the psycho-stimulative perfume composition was added thereto. The resultant mixture was further stirred thoroughly, to thereby form a uniform mixture serving as a bath preparation.

Example 33

Gel-Type Aromatic Product

| Formulation | Amount (parts by mass) |
| --- | --- |
| Carrageenan | 3.0 |
| Propylene glycol | 2.0 |
| Propylparaben | 0.3 |
| The psycho-stimulative perfume composition of Example 12 | 5.0 |
| Ion-exchange water | 89.7 |

<Production Method>

Carrageenan, propylene glycol, and propylparaben were mixed together under stirring while ion-exchange water was added to the mixture. Subsequently, the resultant mixture was heated to about 80° C. under gentle stirring. After the temperature of the mixture had been lowered to about 65° C., the psycho-stimulative perfume composition was added thereto under stirring by means of a homogenizer (3,000 rpm) so as to form a uniform phase. The product was poured into a predetermined container and was allowed to stand for cooling, to thereby produce an aromatic product.

Example 34

Liquid-Type Aromatic Product

| Formulation | Amount (parts by mass) |
| --- | --- |
| 95% Ethanol | 25.0 |
| Surfactant | 5.0 |
| The psycho-stimulative perfume composition of Example 12 | 3.0 |
| Ion-exchange water | 67.0 |

<Production Method>

The above ingredients except for ion-exchange water were mixed together, and ion-exchange water was added thereto under gentle stirring, to thereby form a uniform mixture serving as an aromatic product. In the production, polyoxyethylene nonylphenyl ether (EO-13) was employed as a surfactant.

Example 35

Liquid-Type Deodorant

| Formulation | Amount (parts by mass) |
| --- | --- |
| Deodorant source liquid FS-500M (product of Shiraimatsu Pharmaceutical Co., Ltd.) | 5.0 |
| 95% Ethanol | 10.0 |
| Surfactant | 10.0 |
| The psycho-stimulative perfume composition of Example 11 | 10.0 |
| Ion-exchange water | 65.0 |

<Production Method>

The above ingredients except for ion-exchange water were mixed together, and ion-exchange water was added thereto under gentle stirring, to thereby produce a deodorant (liquid type). In the production, polyoxyethylene nonylphenyl ether (EO-10) was employed as a surfactant.

Example 36

Aerosol-Type Deodorant

| Formulation | Amount (parts by mass) |
| --- | --- |
| Deodorant source liquid FS-500M | 5.0 |
| 95% Ethanol | 20.0 |
| The psycho-stimulative perfume composition of Example 11 | 10.0 |
| Ion-exchange water | 40.0 |
| Liquefied petroleum gas (4 kg/cm$^2$, 20° C.) | 25.0 |

<Production Method>

The above ingredients except for liquified petroleum gas were mixed together under stirring so as to form a uniform mixture, and a predetermined amount of the mixture was placed in an aerosol container. Subsequently, liquified petroleum gas was injected into the aerosol container equipped with a valve, to thereby produce a deodorant (aerosol type).

Example 37

Bath Preparation

| Formulation | Amount (parts by mass) |
| --- | --- |
| Sodium hydrogencarbonate | 70.0 |
| Sodium sulfate anhydrate | 28.8 |
| The psycho-stimulative perfume composition of Example 16 | 1.0 |
| Pigment Y-202-1 | 0.2 |

<Production Method>

The above ingredients except for the perfume composition were stirred by means of a V-type mixer so as to form a uniform mixture, and the psycho-stimulative perfume composition was added thereto. The resultant mixture was further stirred thoroughly, to thereby form a uniform mixture serving as a bath preparation.

Example 38

Gel-Type Aromatic Product

| Formulation | Amount (parts by mass) |
| --- | --- |
| Carrageenan | 3.0 |
| Propylene glycol | 2.0 |
| Propylparaben | 0.3 |
| The psycho-stimulative perfume composition of Example 16 | 5.0 |
| Ion-exchange water | 89.7 |

<Production Method>

Carrageenan, propylene glycol, and propylparaben were mixed together under stirring while ion-exchange water was added to the mixture. Subsequently, the resultant mixture was heated to about 80° C. under gentle stirring. After the temperature of the mixture had been lowered to about 65° C., the psycho-stimulative perfume composition was added thereto under stirring by means of a homogenizer (3,000 rpm) so as to form a uniform phase. The product was poured into a predetermined container and was allowed to stand for cooling, to thereby produce an aromatic product.

Example 39

Liquid-Type Aromatic Product

| Formulation | Amount (parts by mass) |
| --- | --- |
| 95% Ethanol | 25.0 |
| Surfactant | 5.0 |
| The psycho-stimulative perfume composition of Example 16 | 3.0 |
| Ion-exchange water | 67.0 |

<Production Method>

The above ingredients except for ion-exchange water were mixed together, and ion-exchange water was added thereto under gentle stirring, to thereby form a uniform mixture serving as an aromatic product. In the production, polyoxyethylene nonylphenyl ether (EO-13) was employed as a surfactant.

Example 40

Liquid-Type Deodorant

| Formulation | Amount (parts by mass) |
| --- | --- |
| Deodorant source liquid FS-500M (product of Shiraimatsu Pharmaceutical Co., Ltd.) | 5.0 |
| 95% Ethanol | 10.0 |
| Surfactant | 10.0 |
| Perilla aldehyde | 10.0 |
| Ion-exchange water | 65.0 |

<Production Method>

The above ingredients except for ion-exchange water were mixed together, and ion-exchange water was added thereto under gentle stirring, to thereby produce a deodorant (liquid type). In the production, polyoxyethylene nonylphenyl ether (EO-10) was employed as a surfactant.

Example 41

Aerosol-Type Deodorant

| Formulation | Amount (parts by mass) |
| --- | --- |
| Deodorant source liquid FS-500M | 5.0 |
| 95% Ethanol | 20.0 |
| Perilla aldehyde | 10.0 |
| Ion-exchange water | 40.0 |
| Liquefied petroleum gas (4 kg/cm², 20° C.) | 25.0 |

<Production Method>

The above ingredients except for liquified petroleum gas were mixed together under stirring so as to form a uniform mixture, and a predetermined amount of the mixture was placed in an aerosol container. Subsequently, liquified petroleum gas was injected into the aerosol container equipped with a valve, to thereby produce a deodorant (aerosol type).

Example 42

Cream

| Formulation | Amount (mass %) |
| --- | --- |
| Stearic acid | 10.0 |
| Stearyl alcohol | 4.0 |
| Butyl stearate | 8.0 |
| Glyceryl monostearate | 2.0 |

-continued

| Formulation | Amount (mass %) |
|---|---|
| Vitamin E acetate | 0.5 |
| Vitamin A palmitate | 0.1 |
| Macadamia nut oil | 1.0 |
| Tea seed oil | 3.0 |
| Glycerin | 4.0 |
| 1,2-Pentanediol | 3.0 |
| Sodium hyaluronate | 1.0 |
| Potassium hydroxide | 2.0 |
| Magnesium ascorbyl phosphate | 0.1 |
| L-Arginine hydrochloride | 0.01 |
| Trisodium edetate | 0.05 |
| The psycho-stimulative perfume composition of Example 17 | 0.4 |
| Preservative | Suitable amount |
| Purified water | Balance |

<Production Method>

The cream was produced through a routine method.

Example 43

Cream

| Formulation | Amount (mass %) |
|---|---|
| Cetanol | 4.0 |
| Vaseline | 7.0 |
| Isopropyl myristate | 8.0 |
| Squalane | 15.0 |
| Glyceryl monostearate | 2.2 |
| POE(20) sorbitan monostearate | 2.8 |
| Vitamin E nicotinate | 2.0 |
| Glycerin | 10.0 |
| Sodium hyaluronate | 0.02 |
| Dipropylene glycol | 4.0 |
| Sodium pyrrolidonecarboxylate | 1.0 |
| The psycho-stimulative perfume composition of Example 17 | 0.3 |
| Disodium edetate | 0.01 |
| Antioxidant | Suitable amount |
| Preservative | Suitable amount |
| Purified water | Balance |

<Production Method>

The cream was produced through a routine method.

Example 44

Milky Lotion

| Formulation | Amount (mass %) |
|---|---|
| Squalane | 5.0 |
| Oleyl oleate | 3.0 |
| Vaseline | 2.0 |
| Sorbitan sesquioleate | 0.8 |
| POE(20) oleyl ether | 1.2 |
| Evening primrose oil | 0.5 |
| 1,3-Butylene glycol | 4.5 |
| Ethanol | 3.0 |

-continued

| Formulation | Amount (mass %) |
|---|---|
| Carboxyvinyl polymer | 0.2 |
| Potassium hydroxide | 0.1 |
| L-Arginine L-aspartate | 0.01 |
| Salt of Edetic acid | 0.05 |
| The psycho-stimulative perfume composition of Example 15 | 0.3 |
| Preservative | Suitable amount |
| Purified water | Balance |

<Production Method>

The milky lotion was produced through a routine method.

Example 45

Lotion

| Formulation | Amount (mass %) |
|---|---|
| Cetanol | 3.5 |
| POE oleyl alcohol ether | 2.0 |
| 2-Ethylhexyl p-dimethylaminobenzoate | 0.18 |
| 1,3-Butylene glycol | 9.5 |
| Sodium pyrrolidonecarboxylate | 0.5 |
| Nicotinamide | 0.3 |
| Glycerin | 5.0 |
| The psycho-sedative perfume composition of Example 5 | 0.05 |
| Purified water | Balance |

<Production Method>

The lotion was produced through a routine method.

INDUSTRIAL APPLICABILITY

In the present invention, novel components which are acknowledged to have a mental sedative or a mental stimulative effect have been identified. Thus, the present invention provides a psycho-controlling perfume composition containing one or more said components and external compositions and daily-use goods containing the psycho-controlling perfume composition.

The invention claimed is:

1. A psycho-sedating method comprising inhaling one or more components selected from the group consisting of terpinyl butyrate, γ-nonalactone, acetyl isoeugenol, methyl anisate, nerol, chrysanthenone, lyral, lilial, γ-methyl ionone, Iso E Super, Z-3-hexenyl salicylate, limonene, ocimene, helional, linalyl acetate, geranyl acetate, geraniol, hedione, citronellol, and γ-hexalactone, thereby effecting mental sedation.

2. A psycho-stimulating method comprising inhaling one or more components selected from the group consisting of piperitone, isoamyl angelate, phenylethyl angelate, cuminyl alcohol, mentalactone, and ethyl myristate, thereby effecting mental stimulation.

* * * * *